US008586072B2

(12) United States Patent
Weber et al.

(10) Patent No.: US 8,586,072 B2
(45) Date of Patent: Nov. 19, 2013

(54) MEDICAL DEVICES HAVING COATINGS FOR CONTROLLED THERAPEUTIC AGENT DELIVERY

(75) Inventors: Jan Weber, Maastricht (NL); Aiden Flanagan, Galway (IE); Tim O'Connor, Galway (IE); Barry J. O'Brien, Galway (IE); John Clarke, Galway (IE); David McMorrow, Galway (IE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 793 days.

(21) Appl. No.: 11/983,796

(22) Filed: Nov. 9, 2007

(65) Prior Publication Data
US 2009/0123521 A1    May 14, 2009

Related U.S. Application Data

(60) Provisional application No. 60/857,849, filed on Nov. 9, 2006.

(51) Int. Cl.
  *A61F 2/00* (2006.01)
  *A61L 27/30* (2006.01)
  *A61L 31/16* (2006.01)
  *A61N 1/05* (2006.01)

(52) U.S. Cl.
  USPC ............ 424/426; 514/449; 607/115; 977/931

(58) Field of Classification Search
  None
  See application file for complete search history.

(56) References Cited

U.S. PATENT DOCUMENTS

| | | | |
|---|---|---|---|
| 5,733,925 A | 3/1998 | Kunz et al. | |
| 6,712,845 B2 * | 3/2004 | Hossainy | 623/1.42 |
| 6,803,070 B2 | 10/2004 | Weber | |
| 2002/0004060 A1 | 1/2002 | Heublein et al. | |
| 2003/0207145 A1 * | 11/2003 | Anderson et al. | 428/626 |
| 2004/0019143 A1 | 1/2004 | Koloski et al. | |
| 2004/0098089 A1 | 5/2004 | Weber | |
| 2004/0148015 A1 * | 7/2004 | Lye et al. | 623/1.15 |
| 2005/0051763 A1 | 3/2005 | Affinito et al. | |
| 2005/0165439 A1 | 7/2005 | Weber et al. | |
| 2006/0127443 A1 * | 6/2006 | Helmus | 424/423 |
| 2006/0129215 A1 | 6/2006 | Helmus et al. | |
| 2006/0193886 A1 * | 8/2006 | Owens et al. | 424/423 |
| 2006/0229711 A1 | 10/2006 | Yan et al. | |
| 2006/0293563 A1 | 12/2006 | Banik et al. | |
| 2007/0043256 A1 | 2/2007 | Banik | |
| 2007/0224235 A1 * | 9/2007 | Tenney et al. | 424/423 |

FOREIGN PATENT DOCUMENTS

WO    2006104644 A2    10/2006

OTHER PUBLICATIONS

E.K.F. Yim et al., "Significance of synthetic nanostructures in dictating cellular response," Nanomedicine: Nanotechnology, Biology, and Medicine 1, 2005, pp. 10-21.
Viitala R. et al., "Surface properties of in vitro bioactive and non-bioactive sol-gel derived materials," Biomaterials, Aug. 2002, 23,15, pp. 3073-3086.
E.E.L.Swan et al., "Fabrication and evaluation of nanoporous alumina membranes for osteoblast culture," Journal of Biomedical Materials Research Part A, vol. 72A, Issue 3, pp. 288-295, Published Online: Jan. 14, 2005.
Oxford Applied Research, "Nanocluster Deposition Systems—Nanodep60," Downloaded from http://www.oaresearch.co.uk/nanodep60.htm on Nov. 3, 2006.
Mantis Deposition Ltd., "Nanocluster Deposition"; downloaded from http://www.mantisdeposition.com/nanocluster.html on Feb. 2, 2007.
R. D'Aquino, "Good Drug Therapy: It's Not Just the Molecule—It's the Delivery" www.cepmagazin.org. Feb. 2004 CEP.
Chow et al., "Nanostructured Films and Coating by Evaporation, Sputtering, Thermal Spraying, Electro- and Electroless Deposition", in Handbook of Nanophase and Nanostructured Materials, vol. 1. Synthesis, Chapter 9, Zhong Lin Wang, Yi Liu, and Ze Zhang, editors; Kluwer Academic/Plenum Publishers, 2003, pp. 246-272.
"GVD. Simple, Functional, Radical. Nanocoatings for a New Era." Date: at least as early as Nov. 12, 2003, 3 pages.
Jomed starts clinical studes on Tacrolimus-eluting coronary stents. Jan. 14, 2002, 2 pages.
K.K.S. Lau et al., "Hot-wire chemical vapor deposition (HWCVD) of fluorocarbon and organosilicon thin films," Thin Solid Films, 395 (2001) pp. 288-291.
"Debiotech obtains exclusive rights to an innovative drug eluting stent technology" Mar. 7, 2003, 1 page.
T. Desai et al., "Use of Microfabricated 'Nanopore' Membranes as a Rate-Limiting Barrier to Diffusion of Small and Large Molecules: Possible Role in Drug Delivery", BioMems and Nanotechnology World, 2001, 2 pages.
D. A. Lavan et al., Small-scale systems for in vivo drug delivery, Nature Biotechnology, vol. 21, No. 10, Oct. 2003, pp. 1184-1191.
F.J. Martin et al. "Microfabricated Drug Delivery Systems: Concepts to Improve Clinical Benefit," Biomedical Microdevices, Jun. 2001, vol. 3, No. 2, pp. 97-107.
A. Jain et al., "Direct Access to Bicontinuous Skeletal Inorganic Plumber's Nightmare Networks from Block Copolymers," Angew. Chem. Int. Ed., 2005, 44, pp. 1226-1229.

* cited by examiner

*Primary Examiner* — Suzanne Ziska
(74) *Attorney, Agent, or Firm* — Mayer & Williams PC; David B. Bonham

(57) ABSTRACT

According to an aspect of the invention, medical devices are provided, which include a nanoparticle-derived inorganic layer disposed over a least a portion of structure that includes a substrate, and optionally, a therapeutic-agent-containing layer disposed over at least a portion of the substrate. In some embodiments, the inorganic layer is a nanoporous inorganic layer. Other aspects of the invention comprise methods for forming such medical device.

46 Claims, 4 Drawing Sheets

US 8,586,072 B2

MEDICAL DEVICES HAVING COATINGS FOR CONTROLLED THERAPEUTIC AGENT DELIVERY

STATEMENT OF RELATED APPLICATION

This application claims the benefit of U.S. Provisional Application. No. 60/857,849, filed Nov. 9, 2006, the contents of which are hereby incorporated by reference.

TECHNICAL FIELD

This invention relates to medical devices, and more particularly, to medical devices having inorganic coatings that control mass transport of various species, including therapeutic agents, among others.

BACKGROUND OF THE INVENTION

The in-situ delivery of therapeutic agents within the body of a patient is common in the practice of modern medicine. In-situ delivery of therapeutic agents is often implemented using medical devices that may be temporarily or permanently placed at a target site within the body. These medical devices can be maintained, as required, at their target sites for short or prolonged periods of time, in order to deliver therapeutic agents to the target site.

For example, in recent years, drug eluting coronary stents, which are commercially available from Boston Scientific Corp. (TAXUS), Johnson & Johnson (CYPHER) and others, have been widely used for maintaining vessel patency after balloon angioplasty. These products are based on metallic expandable stents with biostable polymer coatings that release antirestenotic drugs at a controlled rate and total dose.

Polymeric coatings for drug release from implantable or insertable devices such as stents may be less desirable with regard to long term vascular compatibility.

iMEDD, Inc. has created silicon membranes with parallel channels ranging from 4 to 50 nm. Diffusion rates of various solutes through such membranes have been measured and conform to zero-order kinetics in some instances. According to iMedd, the membranes can be engineered to control rates of diffusion by adjusting channel width in relation to the size of solutes. When the proper balance is struck, zero-order diffusion kinetics is possible. iMedd has produced a drug delivery device which consists of a drug-filled enclosure which is then fitted with a nanoporous membrane as the only connection between the internal reservoir of the device and the external medium.

SUMMARY OF THE INVENTION

According to an aspect of the invention, medical devices are provided, which include a nanoparticle-derived inorganic layer disposed over a least a portion of structure that includes a substrate, and optionally, a therapeutic-agent-containing layer disposed over at least a portion of the substrate. In some embodiments, the inorganic layer is a nanoporous inorganic layer. In some embodiments, a macroporous inorganic layer is disposed over a therapeutic-agent-containing layer and under a nanoporous inorganic layer.

Other aspects of the invention comprise methods for forming medical devices.

In some embodiments, these methods include accelerating inorganic nanoparticles onto an upper surface of a structure that includes a substrate and, optionally, a therapeutic-agent-containing layer disposed over at least a portion of the substrate. The inorganic nanoparticles are accelerated under conditions such that a layer comprising fused inorganic nanoparticles is formed over the structure.

An advantage of the present invention is that medical devices may be provided, in which the release of therapeutic agents is closely controlled.

Another advantage of the present invention is that medical devices with release-regulating layers may be provided, in which it is not necessary to pass therapeutic agent into or through the layers in order to load the medical devices with the therapeutic agent.

These and other embodiments and advantages of the present invention will become immediately apparent to those of ordinary skill in the art upon review of the Detailed Description and Claims to follow.

DETAILED DESCRIPTION

Figure 1:
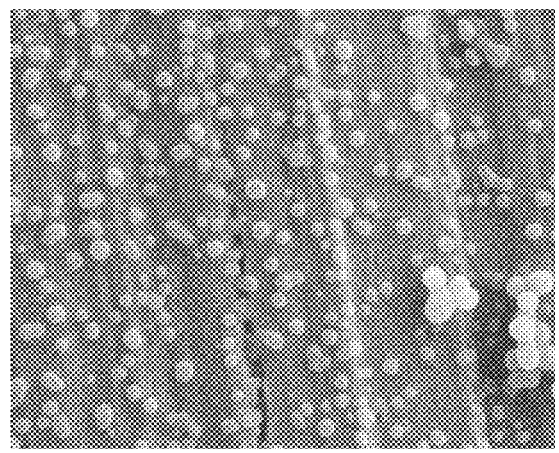
FIG. 1 is an electron micrograph of a discontinuous paclitaxel coating disposed on a metallic substrate.

According to an aspect of the invention, medical devices are provided, which include a nanoparticle-derived inorganic layer disposed over a least a portion of structure that includes a substrate and, optionally, a therapeutic-agent-containing layer (also referred to herein as a "therapeutic layer") disposed over at least a portion of the substrate.

According to another aspect of the invention, a method is provided which includes accelerating inorganic nanoparticles onto an upper surface of a structure that includes a substrate and, optionally, a therapeutic layer disposed over at least a portion of the substrate. The inorganic nanoparticles are accelerated under conditions such that an inorganic layer comprising fused inorganic nanoparticles is formed over the structure.

In some embodiments, the above inorganic layers are nanoporous inorganic layers. For example, various nanoporous inorganic layers are described below in conjunction with the drawings. However, the present invention is not limited to nanoporous inorganic layers. Inorganic layers of any porosity, including non-porous layers, may be employed.

Examples of medical devices benefiting from the present invention vary widely and include implantable or insertable medical devices, for example, stents (including coronary vascular stents, peripheral vascular stents, cerebral, urethral, ureteral, biliary, tracheal, gastrointestinal and esophageal stents), stent coverings, stent grafts, vascular grafts, abdominal aortic aneurysm (AAA) devices (e.g., AAA stents, AAA grafts), vascular access ports, dialysis ports, catheters (e.g., urological catheters or vascular catheters such as balloon catheters and various central venous catheters), guide wires, balloons, filters (e.g., vena cava filters and mesh filters for distil protection devices), embolization devices including cerebral aneurysm filler coils (including Guglilmi detachable coils and metal coils), septal defect closure devices, myocardial plugs, patches, pacemakers, lead coatings including coatings for pacemaker leads, defibrillation leads, and coils, ventricular assist devices including left ventricular assist hearts and pumps, total artificial hearts, shunts, valves including heart valves and vascular valves, anastomosis clips and rings, cochlear implants, tissue bulking devices, and tissue engineering scaffolds for cartilage, bone, skin and other in vivo tissue regeneration, sutures, suture anchors, tissue staples and ligating clips at surgical sites, cannulae, metal wire ligatures, urethral slings, hernia "meshes", artificial ligaments, orthopedic prosthesis such as bone grafts, bone plates, fins and fusion devices, joint prostheses, orthopedic fixation devices such as interference screws in the ankle, knee, and hand areas, tacks for ligament attachment and meniscal repair, rods and pins for fracture fixation, screws and plates for craniomaxillofacial repair, dental implants, or other devices that are implanted or inserted into the body and from which therapeutic agent is released.

Thus, while the devices of the invention in some embodiments may simply provide for controlled species transport (e.g., the controlled release of one or more therapeutic agents as a dosage form, controlling flow of ions into and out of an electroactive polymer, etc.), in other embodiments, the medical devices of the invention are configured to provide a therapeutic function beyond controlled species transport, for instance, providing mechanical, thermal, magnetic and/or electrical functions within the body, among other many possible functions.

The medical devices of the present invention include, for example, implantable and insertable medical devices that are used for systemic treatment, as well as those that are used for the localized treatment of any mammalian tissue or organ. Non-limiting examples are tumors; organs including the heart, coronary and peripheral vascular system (referred to overall as "the vasculature"), the urogenital system, including kidneys, bladder, urethra, ureters, prostate, vagina, uterus and ovaries, eyes, ears, spine, nervous system, lungs, trachea, esophagus, intestines, stomach, brain, liver and pancreas, skeletal muscle, smooth muscle, breast, dermal tissue, cartilage, tooth and bone.

As used herein, "treatment" refers to the prevention of a disease or condition, the reduction or elimination of symptoms associated with a disease or condition, or the substantial or complete elimination of a disease or condition. Subjects are vertebrate subjects, more typically mammalian subjects including human subjects, pets and livestock.

In certain embodiments, the medical articles have sustained therapeutic agent release profiles. By "sustained release profile" is meant a release profile in which less than 25% of the total release from the medical article that occurs over the entire course of administration occurs over the first 1 day (or in some embodiments, over the first 2, 4, 8, 16, 32, 64, 128 or even more days) of administration. This means that more than 75% of the total release from the medical device will occur after the device has been administered for the same period.

Substrate materials for the medical devices of the present invention may vary widely in composition and are not limited to any particular material. They can be selected from a range of biostable materials and biodisintegrable materials (i.e., materials that, upon placement in the body, are dissolved, degraded, resorbed, and/or otherwise removed from the placement site), including (a) organic materials (i.e., materials containing organic species, typically 50 wt % or more, for example, from 50 wt % to 75 wt % to 90 wt % to 95 wt % to 97.5 wt % to 99 wt % or more) such as polymeric materials (i.e., materials containing polymers, typically 50 wt % or more polymers, for example, from 50 wt % to 75 wt % to 90 wt % to 95 wt % to 97.5 wt % to 99 wt % or more) and biologics, (b) inorganic materials (i.e., materials containing inorganic species, typically 50 wt % or more, for example, from 50 wt % to 75 wt % to 90 wt % to 95 wt % to 97.5 wt % to 99 wt % or more), such as metallic inorganic materials (i.e., materials containing metals, typically 50 wt % or more, for example, from 50 wt % to 75 wt % to 90 wt % to 95 wt % to 97.5 wt % to 99 wt % or more) and non-metallic inorganic materials (i.e., materials containing non-metallic inorganic materials, typically 50 wt % or more, for example, from 50 wt % to 75 wt % to 90 wt % to 95 wt % to 97.5 wt % to 99 wt % or more) (e.g., including carbon, semiconductors, glasses and ceramics, which may contain various metal- and non-metal-oxides, various metal- and non-metal-nitrides, various metal- and non-metal-carbides, various metal- and non-metal-borides, various metal- and non-metal-phosphates, and various metal- and non-metal-sulfides, among others), and (c) hybrid materials (e.g., hybrid organic-inorganic materials, for instance, polymer/metallic inorganic and polymer/non-metallic inorganic hybrids).

Specific examples of inorganic non-metallic materials may be selected, for example, from materials containing one or more of the following: metal oxide ceramics, including aluminum oxides and transition metal oxides (e.g., oxides of titanium, zirconium, hafnium, tantalum, molybdenum, tungsten, rhenium, iron, niobium, and iridium); silicon; silicon-based ceramics, such as those containing silicon nitrides, silicon carbides and silicon oxides (sometimes referred to as glass ceramics); calcium phosphate ceramics (e.g., hydroxyapatite); carbon; and carbon-based, ceramic-like materials such as carbon nitrides.

Specific examples of metallic materials may be selected, for example, from metals such as gold, iron, niobium, platinum, palladium, iridium, osmium, rhodium, titanium, tantalum, tungsten, ruthenium, zinc, and magnesium, among others, and alloys such as those comprising iron and chromium (e.g., stainless steels, including platinum-enriched radiopaque stainless steel), niobium alloys, titanium alloys, alloys comprising nickel and titanium (e.g., Nitinol), alloys comprising cobalt and chromium, including alloys that comprise cobalt, chromium and iron (e.g., elgiloy alloys), alloys comprising nickel, cobalt and chromium (e.g., MP 35N), alloys comprising cobalt, chromium, tungsten and nickel (e.g., L605), alloys comprising nickel and chromium (e.g., inconel alloys), and biodisintegrable alloys including alloys of magnesium, zinc and/or iron (and their alloys with combinations of Ce, Ca, Al, Zr and Li), among others (e.g., alloys of magnesium including its alloys that comprises one or more of Fe, Ce, Al, Ca, Zn, Zr and Li, alloys of iron including its alloys that comprise one or more of Mg, Ce, Al, Ca, Zn, Zr and Li, alloys of zinc including its alloys that comprise one or more of Fe, Mg, Ce, Al, Ca, Zr and Li, etc.).

Specific examples of organic materials include polymers (biostable or biodisintegrable) and other high molecular weight organic materials, and may be selected, for example, from suitable materials containing one or more of the following: polycarboxylic acid polymers and copolymers including polyacrylic acids; acetal polymers and copolymers; acrylate and methacrylate polymers and copolymers (e.g., n-butyl methacrylate); cellulosic polymers and copolymers, including cellulose acetates, cellulose nitrates, cellulose propionates, cellulose acetate butyrates, cellophanes, rayons, rayon triacetates, and cellulose ethers such as carboxymethyl celluloses and hydroxyalkyl celluloses; polyoxymethylene polymers and copolymers; polyimide polymers and copolymers such as polyether block imides, polyamidimides, polyesterimides, and polyetherimides; polysulfone polymers and copolymers including polyarylsulfones and polyethersulfones; polyamide polymers and copolymers including nylon 6,6, nylon 12, polyether-block co-polyamide polymers (e.g., Pebax® resins), polycaprolactams and polyacrylamides; resins including alkyd resins, phenolic resins, urea resins, melamine resins, epoxy resins, allyl resins and epoxide resins; polycarbonates; polyacrylonitriles; polyvinylpyrrolidones (cross-linked and otherwise); polymers and copolymers of vinyl monomers including polyvinyl alcohols, polyvinyl halides such as polyvinyl chlorides, ethylene-vinylacetate copolymers (EVA), polyvinylidene chlorides, polyvinyl ethers such as polyvinyl methyl ethers, vinyl aromatic polymers and copolymers such as polystyrenes, styrene-maleic anhydride copolymers, vinyl aromatic-hydrocarbon copolymers including styrene-butadiene copolymers, styrene-ethylene-butylene copolymers (e.g., a polystyrene-polyethylene/butylene-polystyrene (SEBS) copolymer, available as Kraton® G series polymers), styrene-isoprene copolymers (e.g., polystyrene-polyisoprene-polystyrene), acrylonitrile-styrene copolymers, acrylonitrile-butadiene-styrene copolymers, styrene-butadiene copolymers and styrene-isobutylene copolymers (e.g., polyisobutylene-polystyrene block copolymers such as poly(styrene-b-isobutylene-b-styrene) or SIBS, which is described, for instance, in U.S. Pat. No. 6,545,097 to Pinchuk et al.), polyvinyl ketones, polyvinylcarbazoles, and polyvinyl esters such as polyvinyl acetates; polybenzimidazoles; ionomers; polyalkyl oxide polymers and copolymers including polyethylene oxides (PEO); polyesters including polyethylene terephthalates, polybutylene terephthalates and aliphatic polyesters such as polymers and copolymers of lactide (which includes lactic acid as well as d-, l- and meso lactide), epsilon-caprolactone, glycolide (including glycolic acid), hydroxybutyrate, hydroxyvalerate, para-dioxanone, trimethylene carbonate (and its alkyl derivatives), 1,4-dioxepan-2-one, 1,5-dioxepan-2-one, and 6,6-dimethyl-1,4-dioxan-2-one (a copolymer of polylactic acid and polycaprolactone is one specific example); polyether polymers and copolymers including polyarylethers such as polyphenylene ethers, polyether ketones, polyether ether ketones; polyphenylene sulfides; polyisocyanates; polyolefin polymers and copolymers, including polyalkylenes such as polypropylenes, polyethylenes (low and high density, low and high molecular weight), polybutylenes (such as polybut-1-ene and polyisobutylene), polyolefin elastomers (e.g., santoprene), ethylene propylene diene monomer (EPDM) rubbers, poly-4-methyl-pen-1-enes, ethylene-alpha-olefin copolymers, ethylene-methyl methacrylate copolymers and ethylene-vinyl acetate copolymers; fluorinated polymers and copolymers, including polytetrafluoroethylenes (PTFE), poly(tetrafluoroethylene-co-hexafluoropropene) (FEP), modified ethylene-tetrafluoroethylene copolymers (ETFE), and polyvinylidene fluorides (PVDF); silicone polymers and copolymers; polyurethanes; p-xylylene polymers; polyiminocarbonates; copoly(ether-esters) such as polyethylene oxide-polylactic acid copolymers; polyphosphazines; polyalkylene oxalates; polyoxaamides and polyoxaesters (including those containing amines and/or amido groups); polyorthoesters; biopolymers, such as polypeptides, proteins, polysaccharides and fatty acids (and esters thereof), including fibrin, fibrinogen, collagen, elastin, chitosan, gelatin, starch, and glycosaminoglycans such as hyaluronic acid; as well as blends and further copolymers of the above.

As indicated above, in some embodiments, the invention provides medical devices in which at least one therapeutic-agent-containing layer ("therapeutic layer") is disposed over at least a portion of a substrate.

The therapeutic layers may contain, for example, from 1 wt % or less to 2 wt % to 5 wt % to 10 wt % to 25 wt % to 50 wt % to 75 wt % to 90 wt % to 95 wt % to 97.5 wt % to 99 wt % or more of a single therapeutic agent or of a mixture of therapeutic agents within the layer. Examples of materials other than therapeutic agent(s) which can be used to form therapeutic layers include materials that serve as reservoirs/binders/matrices for the therapeutic agent, including organic materials (e.g., polymeric materials, etc.) and inorganic materials (e.g., metallic inorganic materials and non-metallic inorganic materials) which may be selected, for example, from those listed above, among others, and porous particles within which therapeutic agent may be absorbed (e.g., porous silica particles). For example, the therapeutic layers may comprise one or more therapeutic agents disposed within porous or nonporous reservoir layers formed, for instance, from organic materials, inorganic materials, or hybrids thereof.

Layers can be provided over an underlying substrate at a variety of locations, and in a variety of shapes (e.g., in desired patterns, for instance, using suitable application techniques and/or masking techniques). As used herein a "layer" of a given material is a region of that material whose thickness is small compared to both its length and width. As used herein a layer need not be planar, for example, taking on the contours of an underlying substrate. A layer can be discontinuous, providing only partial coverage of the underlying substrate. Terms such as "film," "layer" and "coating" may be used interchangeably herein.

Therapeutic layer thicknesses may vary widely, typically ranging from 10 nm to 25 nm to 50 nm to 100 nm to 250 nm to 100 nm to 500 nm to 1000 nm (1 µm) or more in thickness.

Therapeutic layers may be disposed over substrates using any suitable method known in the art. These methods include methods of forming substantially pure therapeutic agent layers, for example, contacting the substrate with a liquid that comprises a solvent and a therapeutic agent (e.g., in dissolved or dispersed form) or deposition of dry or semi-dry particles of therapeutic agent on the surface of the substrate. This may be accomplished, for example, through spray coating, ink jet droplet deposition, ultrasonic spray coating, electrohydrodynamic coating, or dipping or roll-coating the device in a suspension or solution of the therapeutic agent, among other methods.

As a specific example, FIG. 1 is a micrograph illustrating an embodiment of the invention wherein discontinuous layer of paclitaxel (in the form of nanoparticles having a diameter of about 300 nm) has been deposited on a stainless steel substrate. The stent is spray coated in a 0.005% to 10% solution of the drug (preferably 0.05% to 1% solution) and allowed to dry for 1-60 seconds. For smaller drug particles, the drying is accelerated by a current of warm air or using more volatile solvents in the solution.

In many embodiments, therapeutic layers are formed from therapeutic-agent-containing fluids (e.g., solutions, dispersions, melts, etc.) In certain embodiments, a layer is formed that comprises at least one therapeutic agent and at least one additional agent (e.g., a polymer and/or porous particle, etc.). For example, where the additional agent(s) comprises one or more polymer(s) having thermoplastic characteristics, a variety of standard thermoplastic processing techniques may be used to form the therapeutic layer. Using these techniques, a therapeutic layer can be formed, for instance, by (a) first providing a melt that contains thermoplastic polymer(s), therapeutic agent(s), and any other additional agent(s), and (b) subsequently cooling the melt. As another example, solvent-based techniques may be used to form the therapeutic layer. Using these techniques, therapeutic layers can be formed, for instance, by (a) first providing a solution or dispersion that contains one or more solvent species, therapeutic agent(s) and any additional agents, and (b) subsequently removing the solvent species.

Examples of techniques wherein fluids (e.g., melts, solutions, dispersions, etc., containing one or more therapeutic agent and any additional agents) may be applied to a substrate include spin coating techniques, web coating techniques, spraying techniques, dipping techniques, roll coating techniques, techniques involving coating via mechanical suspension including air suspension, techniques in which fluid is selectively applied to a substrate, for example, ink jet techniques or techniques involving the use of an applicator such as a brush, roller, pen, etc., electrostatic techniques, and combinations of these processes, among others. In some embodiments, the substrate is masked prior to application of a therapeutic-agent-containing fluid.

As noted above, in one aspect, the invention provides medical devices in which at least one inorganic layer is disposed over at least a portion of a structure that comprises a substrate, and in some embodiments, further comprises at least one therapeutic layer disposed over at least a portion of a substrate. In the medical devices of the present invention, transport of chemical species (e.g., ions, therapeutic agents, etc.) is at least partially regulated by the inorganic layers.

Inorganic layers for use in the present invention may vary widely in composition and are not limited to any particular inorganic material. They can be selected from a wide range of biodisintegrable and biostable inorganic materials, such as suitable members of the inorganic materials listed above, including metallic and non-metallic inorganic materials, as well as hybrids of the same, among others. Inorganic layers in accordance with the present invention may be, for example, biostable, partially biodisintegrable, or fully biodisintegrable.

In some embodiments, inorganic layers in accordance with the present invention are nanoporous. In accordance with the International Union of Pure and Applied Chemistry (IUPAC), a "nanopore" is a pore having a width that does not exceed 50 nm (e.g., from 0.5 nm or less to 1 nm to 2.5 nm to 5 nm to 10 nm to 25 nm to 50 nm). As used herein, nanopores include "micropores," which are pores having a width that does not exceed 2 nm, and "mesopores," which are range from 2 to 50 nm in width. As used herein, "macropores" are larger than 50 nm in width and are thus not nanopores. In the present invention, "nanopores" may further embrace pores up to 1 μm in width, but only where this particular definition is explicitly invoked.

As used herein a "porous" layer is a layer that contains pores. A "nanoporous layer" is a layer that contains nanopores. Nanoporous layers may further comprise some pores that are not nanopores; for example, a nanoporous layer may further comprise macropores. Typically at least 50% by number of the pores within a nanoporous layer are nanopores.

Nanopores are known to promote cell adhesion. See, e.g., the review by E. K. F. Yim et al., "Significance of synthetic nanostructures in dictating cellular response," *Nanomedicine: Nanotechnology, Biology, and Medicine* 1 (2005) 10-21, which reports that smooth muscle cells and endothelial cells have improved cell adhesion and proliferation on nano-patterned surfaces. Both types of cells were sensitive to nanotopography. Yim et al. report improved adhesion and growth for endothelial cells on a substrate with 13 nm high islands relative to 35 and 95 nm high islands. Endothelial cells were also susceptible to surface chemistry. See also, e.g., Viitala R. et al., "Surface properties of in vitro bioactive and non-bioactive sol-gel derived materials," Biomaterials. 2002 August; 23(15): 3073-86 and E. E. L. Swan et al., "Fabrication and evaluation of nanoporous alumina membranes for osteoblast culture," *Journal of Biomedical Materials Research Part A*, Volume 72A, Issue 3, Pages 288-295, Published Online: 14 Jan. 2005.

As discussed below, in accordance with an aspect of the invention, inorganic layers are formed from inorganic nanoparticles, which may be, for example, biodisintegrable inorganic nanoparticles, biostable inorganic nanoparticles, or a combination of biodisintegrable and biostable inorganic nanoparticles.

As used herein, a "nanoparticle" is a particle having a width that does not exceed 1 μm, for example, ranging from 2 nm or less to 4 nm to 8 nm to 10 nm to 15 nm to 20 nm to 25 nm to 35 nm to 50 nm to 100 nm to 150 nm to 250 nm to 500 nm to 1000 nm in width.

For instance, in one idealized scenario, where a porous structure is formed from closed-packed microspheres of identical size, the pores that are created (which correspond to interstices between the packed microspheres) have a minimum width that is about ⅓ the diameter of the microspheres. Thus, in certain embodiments, particles may be selected which have a diameter that is about 3 times (e.g., 3 times or somewhat more, to account for pore shrinkage due to fusion of the particles as discussed below) the hydrated diameter of the therapeutic agent. As a specific example, for paclitaxel, the nanoparticle diameter may range from 8 to 15 nm, among other values.

The thickness of the inorganic layers for use in the present invention may vary widely, for example, ranging from 5 nm to 20 μm in layer thickness, among other values. In certain embodiments, the layer thicknesses will depend upon the size of the inorganic nanoparticles from which the inorganic layer is formed, ranging, for example, from 3 to 5 to 7 to 10 to 15 to 20 to 50 to 75 to 100 or more times the nanoparticle diameter.

Preferred methods of forming inorganic layers in accordance with the present invention include those wherein metallic and/or non-metallic inorganic nanoparticles are accelerated and directed onto upper surfaces of substrate structures that may optionally include therapeutic layers, thereby forming inorganic layers over the substrate structures.

For example, in some embodiments, the nanoparticles are charged nanoparticles, which are accelerated onto the substrate structure surfaces by subjecting them to an electric field. As discussed below, the trajectory of the nanoparticles may be further influenced through the use of a secondary electric field or a magnetic field, where desired.

In some embodiments, the nanoparticles are magnetic or ferromagnetic nanoparticles, which are accelerated onto the substrate structure surfaces by subjecting them to a suitable magnetic field. As discussed below, the trajectory of the nanoparticles may be further influenced through the use of a secondary magnetic field, where desired.

In general, such techniques are performed in a vacuum environment. As a specific example, the Mantis Deposition Ltd. system described below is operated at about $5 \times 10^{-5}$ mbar, although the precise operating pressure used will vary widely, depending on the specific process and system that is employed, among other factors.

Without wishing to be bound by theory, when nanoparticles are accelerated towards a surface (e.g., in a magnetic field, electrical field, etc.), melting can be induced upon landing by imparting them with sufficient kinetic energy. As seen from the above, there are various ways to accelerate nanoparticles toward a therapeutic-agent-coated substrate. For example, in embodiments where charged nanoparticles are accelerated using an electric field, a low applied voltage will create a small electric field which lands them on the substrate with little or no thermal effects. Higher applied voltages, however, will result in greater field strengths, which if sufficiently great will result in a transformation of kinetic energy into heat in an amount sufficient to melt the nanoparticles slightly together, leaving gaps between the particles. Similarly, in embodiments where magnetic or paramagnetic nanoparticles are accelerated using a magnetic field, a low magnetic field strength will just land the nanoparticles on the surface with little or no thermal effects, whereas higher magnetic field strengths will result in the transformation of kinetic energy into heat sufficient to melt the nanoparticles slightly together, leaving gaps between the particles. Even higher field strengths (e.g., magnetic, electrical, etc.) will solidify the individual particles into a solid material without gaps. In some embodiments, adhesion of the nanoparticles to the substrate, to the drug layer and/or to one another each other can be tuned (e.g., by the extent of acceleration). Moreover, structures can be made tough and adherent or soft and friable.

Where porous inorganic layers are formed, the size distribution of the nanoparticles may have a large effect on the pore-size distribution, with larger particles capable of creating larger pores, which pore sizes may be further tailored through the adjustment of field strength. Sustained drug release may be promoted by creating a uniform porosity throughout the nanoporous layer, which will depend upon both the initial size of the particles as well as upon the melting effect that arises from the field strength.

In some embodiments, a soft primer coating (e.g., formed from a soft metal such as gold, or another soft metal or soft metal alloy) is created on the surface of a medical device that has a harder surface material (e.g., a stent, such as a stainless steel stent), for example, by physical vapor deposition (PVD) or by laser pulse deposition, among other techniques, in order to achieve improved penetration of the nanoparticles and therefore improved adhesion of the inorganic layer to the device surface. In these embodiments, lower acceleration of the nanoparticles is required for adhesion and a more porous structure may be achieved. Without a relatively soft primer coating, the porosity created may be compromised by the adhesion required, in some cases.

As a specific example, a system for performing nanoparticle deposition along the lines described above is available from Mantis Deposition Ltd., Thame, Oxfordshire, United Kingdom, who market a high-pressure magnetron sputtering source which is able to generate nanoparticles from a sputter target with as few as 30 atoms up to those with diameters exceeding 15 nm. The size of the nanoparticles is affected by several parameters, including the nanoparticle material, the distance between the magnetron surface and the exit aperture (e.g., larger distances have been observed to create larger nanoparticles), gas flow (e.g., higher gas flows have been observed to create smaller nanoparticle sizes), and gas type (e.g., helium has been observed to produce smaller particles than argon). For a particular setting, the size distribution can be measured using a linear quadrapole device placed after the exit aperture of the magnetron chamber. The quadrapole device can also be used in-line to select a narrow nanoparticle size range for deposition. Systems like the Mantis Deposition Ltd. system can produce nanoparticles, a large fraction of which of which (approximately 40% to 80%) have a charge of one electron. Consequently, a magnetic field or a secondary electric field can be used to separate particles of similar weight from one another (because lighter particles are deflected to a greater degree in a given field than are the larger particles of the same charge). For example, the above Mantis Deposition Ltd. system is able to produce charge nanoparticle streams with a very narrow mass distribution. Moreover, it is possible to accelerate the negatively charged particles onto a positively biased surface in order to impact the particles on the surface with elevated kinetic energy. A positively biased grid may also be used to accelerate the particles, allowing the particles to pass through holes in the grid and impinge on the surface. By altering the bias voltage from low to high values the deposited film changes from porous loosely bound nanoparticles to a solid film of metal. A system similar to the Mantis system can be obtained from Oxford Applied Research, Witney, Oxon, UK. When using a system like the Mantis Deposition Ltd. system, it has been found that the bias voltage (which may vary, for example, from 10 V to 5000 V) and the particle size (which may vary, for example, from 0.7 nm to 25 nm) has a significant effect upon drug release, with higher voltages and smaller particle sizes yielding coatings with reduced drug release.

A further system for accelerating inorganic nanoparticles onto a surface is described in U.S. Pat. No. 6,803,070 to Weber, in which is described an apparatus and method for embedding particles into the polymer matrix of a medical device are disclosed. The apparatus may include an electrostatic outlet (e.g., spray nozzle) adapted to direct a stream of nanoparticles dissolved in a solution toward a positive outlet. A medical device, mounted onto an electrode, may then be placed into or proximate the stream such that upon energizing the electrode (and thus creating an electric field), charged particles are redirected from the outlet toward the electrode. As noted in this patent, by spacing the electrode and energizing the electrode appropriately, the charged particles may be accelerated to a degree sufficient to cause the charged particles to embed themselves into the polymer matrix of the medical device.

In the present invention, on the other hand, charged nanoparticles may be accelerated onto an underlying structure (e.g., one that includes a substrate and, optionally, at least one therapeutic-agent-containing layer disposed over at least a portion of the substrate) using a technique like that described in U.S. Pat. No. 6,803,070 to Weber with an electric field strength that is sufficiently great to fuse the nanoparticles to one another.

As seen from the above, because the nanoparticles from systems such as those above are charged, they can be accelerated within the system by means of an electric field. Moreover, due to the fact that the amount of energy needed to melt the individual nanoparticles is relatively low compared to the energy needed to increase the bulk temperature of underlying substrate structure, this process is effectively performed at or near room temperature.

Because inorganic layers can be formed at or near room temperature, such layers can be deposited upon a wide range of materials including therapeutic agents, polymeric materials, metallic materials, non-metallic inorganic materials, or hybrids thereof, among others.

As an example of the latter, radiopaque or magnetic particles may be provided within a polymeric medical device (e.g., a biodisintegrable polymeric stent, etc.) and used as a substrate. Where radiopaque or magnetic nanoparticles are employed, due to the fact that the particles are very small in size, there should be no negative effect once the stent disintegrates.

Whatever specific system is chosen, the result should be that nanoparticles are provided with a size and a kinetic energy suitable to create an inorganic layer of interconnected nanoparticles.

Where charged particles are mixed with uncharged nanoparticles, the uncharged nanoparticles may be separated, for example, by adding a magnetic field or a secondary electric field perpendicular to the stream of nanoparticles flowing in the primary electric field. This will exert a force on the stream of charged nanoparticles, causing the stream of charged nanoparticles to bend. In this way, it is possible to position a substrate structure at a location such that it is struck only by accelerated charged elements, rather than uncharged elements. As noted above, this effect can further be employed (particularly where the particles are all of the same charge) to produce streams of nanoparticles having a narrow size distribution.

It is further noted that systems can be created which provide a changing secondary field (e.g., an electric or magnetic field that acts to deflect/bend the particle stream created by a primary electric or magnetic field). For example, such a system can induce a continuously changing impact direction at a substrate (e.g., by bending the particle stream). Such as system is suitable for the coating of complex 3-D structures, for example, allowing the charged particles to strike the substrate at varying angles, resulting better coverage (e.g., reducing or avoid shadow effects).

It may be desirable to change the orientation of the substrate structure relative to the charged particle stream. For example, a tubular medical device such as a stent may be axially rotated (and, optionally, reciprocated longitudinally, e.g., where the size of the charged particle stream is small and/or where it is non-uniform) while exposing it to the charged particle stream.

As discussed above, in certain embodiments of the invention, inorganic layers can be deposited after the drug has been deposited onto a device substrate. In other technologies (see, e.g., Pub. No. US 2004/0148015 to Setagon, Inc.), one makes the inorganic layer nanoporous before loading the drug, as the drug would otherwise encounter harsh processing conditions. Moreover, where an inorganic layer is deposited over a therapeutic-agent-containing layer in accordance with the present invention, there is essentially no drug is present on the outside of the inorganic layer after it is formed. Where one post-loads the drug into nanoporous inorganic layers made by other technologies, drug will remain on the outside of the layer. This feature of the present invention allows one to avoid an initial spike in drug release in certain embodiments (e.g., to get better cell response). Furthermore, as discussed in more detail below, the process of the invention allows multiple drug layers and multiple inorganic layers of varying composition to be deposited, which would not be possible with many other technologies.

As noted above, in some embodiments, inorganic layers are formed from biostable inorganic nanoparticles, for example, biostable non-metallic inorganic nanoparticles formed from suitable members of those described above for use in substrates, among others (e.g., titanium oxide, iridium oxide, aluminum oxide, silicon carbide, silicon nitride, titanium nitride, titanium oxy-nitride, etc.); biostable metallic nanoparticles formed from suitable metals described above for use in substrates, among others (e.g., titanium, iridium, tantalum, platinum, gold, niobium, molybdenum, rhenium, etc.); biostable metallic nanoparticles formed from suitable metal alloys described above for use in substrates, among others (e.g., stainless steel, platinum-enriched radiopaque stainless steel, niobium alloys, titanium alloys, nitinol, etc.); and combinations thereof.

As also noted above, in some embodiments, inorganic layers are formed from biodisintegrable inorganic nanoparticles, for example, biodisintegrable non-metallic inorganic nanoparticles formed from suitable members of those described above for use in substrates among others (e.g., calcium carbonates, magnesium carbonates, etc.); biodisintegrable metallic nanoparticles formed from suitable metals described above for use in substrates among others (e.g., iron, magnesium, zinc, etc.); biodisintegrable metallic nanoparticles formed from suitable metal alloys described above for use in substrates, among others (e.g., alloys of magnesium including its alloys that comprises one or more of Fe, Ce, Al, Ca, Zn, Zr and Li, alloys of iron including its alloys that comprise one or more of Mg, Ce, Ca, Zn, Zr and Li, alloys of zinc including its alloys that comprise one or more of Fe, Mg, Ce, Ca, Zr and Li, etc.); and combinations thereof.

In some embodiments, inorganic layers are formed from biocatalytic nanoparticles, for example, biocatalytic metallic nanoparticles such as iridium and platinum, among others, as well as combinations thereof.

In some embodiments, inorganic layers are formed from a combination of two or more of the following: biostable nanoparticles, biodisintegrable nanoparticles, and biocatalytic nanoparticles.

Figure 2:
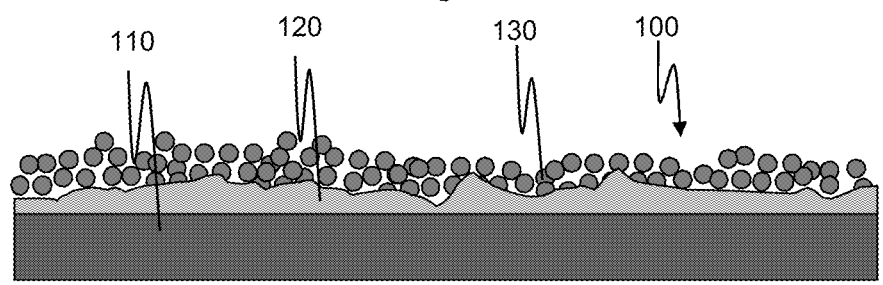
FIGS. 2-7 are schematic cross-sectional illustrations of medical devices in accordance with various embodiments of the invention.

In some embodiments at least some of the nanoparticles have the same composition as the underlying medical device substrate. Specific examples include iridium, tantalum, titanium, cobalt, iron, zinc, gold, alloys containing two or more of the same, stainless steel and nitinol. Several specific embodiments of the invention will now be described in conjunction with the drawings. Referring now to FIG. 2, there is shown therein a schematic cross-sectional illustration of a medical device 100 which includes a biostable or biodegradable medical device substrate 110 (e.g., a biostable or biodisintegrable metallic substrate), a continuous therapeutic layer 120 (e.g., a layer of paclitaxel) disposed on the substrate 110, and a biostable or biodisintegrable inorganic nanoparticle-derived nanoporous layer 130 disposed on the therapeutic layer 120. For example the layer 130 may be a biodisintegrable layer formed from nanoparticles of magnesium, iron, zinc, or their alloys with themselves or other elements. In such a system, the pore size would be expected to increase over time as the layer 130 biodisintegrates, with the entire biodisintegrable layer 130 being ultimately removed in vivo (e.g., dissolved, degraded, resorbed, and/or otherwise removed), along with any remnant of the therapeutic layer 120 (assuming it is biodisintegrable).

Figure 3:
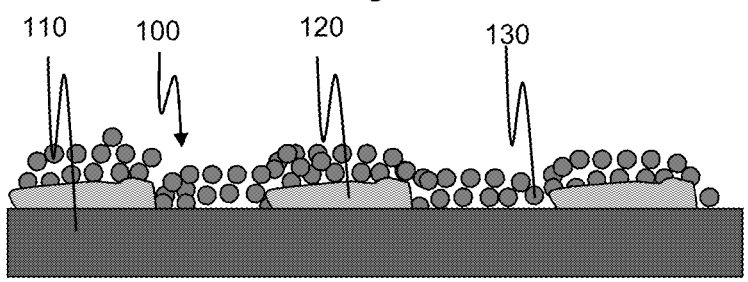

Similar to FIG. 2, there is schematically illustrated in FIG. 3 a cross-section of a medical device 100 which includes a biostable or biodisintegrable medical device substrate 110, a therapeutic layer 120 (e.g., a paclitaxel layer) disposed on the substrate 110, and a biostable or biodisintegrable nanoparticle-derived nanoporous layer 130 disposed on the therapeutic layer 120. Unlike FIG. 2 in which the therapeutic layer 120 is continuous, the therapeutic layer 120 of FIG. 3 is discontinuous. Such a discontinuous therapeutic layer 120 may be formed directly, for example, by depositing non-connected clusters of therapeutic agent (see, e.g., FIG. 1 discussed above) or by forming a continuous therapeutic layer and removing selected portions of the layer. Because the therapeutic layer 120 is non-continuous, the nanoporous layer 130 is fused to the underlying substrate 110 at those positions where the substrate 110 is not covered by the therapeutic layer 120. In certain embodiments, the overlying nanoporous layer 130 is formed from a material that is the same as that of the underlying substrate 110. In certain embodiments, the substrate is provided with a soft metal primer coating.

Figure 4:
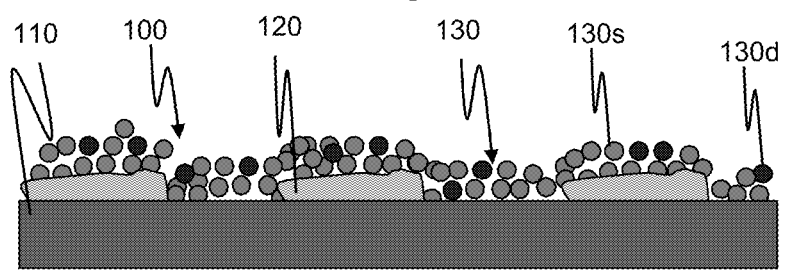

FIG. 4 schematically illustrates a cross-section of a medical device 100 which includes a biostable or biodisintegrable medical device substrate 110, a discontinuous therapeutic layer 120 disposed on the substrate 110, and a nanoporous layer 130 formed from a mixture of biostable nanoparticles 130s and biodisintegrable nanoparticles 130d disposed on the therapeutic layer 120 and the substrate 110. Due to the presence of the nanoparticles 130d, the nanoporous layer 130 is partially biodegradable. This embodiment is useful, for example, where one wishes to increase the porosity of the layer over time (e.g., to increase the release rate of a therapeutic agent, etc.), yet ultimately retain a porous structure (e.g., a nanoporous structure).

Figure 5:
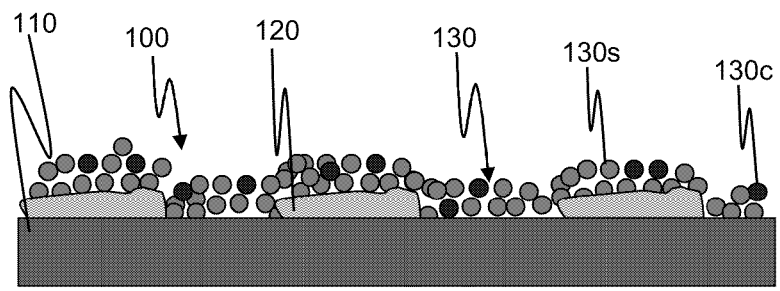

FIG. 5 schematically illustrates a cross-section of a medical device 100 which includes a biostable or biodisintegrable medical device substrate 110, a discontinuous therapeutic layer 120 disposed on the substrate 110, and a nanoporous layer 130 formed from a mixture of biostable nanoparticles 130s and catalytic nanoparticles 130c disposed on the therapeutic layer 120 and the substrate 110. Due to the presence of the nanoparticles 130c, the nanoporous layer 130 has a catalytic function in addition to a therapeutic-agent-releasing function.

Additional embodiments of the invention comprise two or more therapeutic-agent-containing layers separated by one or more nanoparticle-derived inorganic layers. The therapeutic-agent-containing layers may comprise the same or different therapeutic agents, the same or different optional agents (e.g., porous or nonporous matrix/reservoir layers formed from polymeric materials, inorganic materials, or hybrids thereof, within which one or more therapeutic agents are located, etc.), and so forth. The inorganic layers may comprise the same or different compositions, the same or different pores sizes, and so forth.

Figure 6:
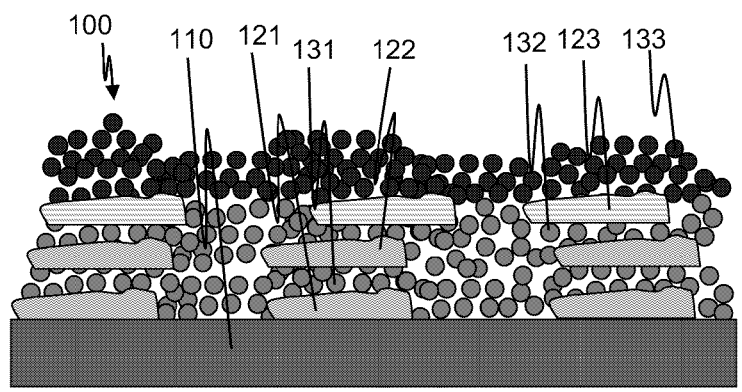

FIG. 6 schematically illustrates a cross-section of a medical device 100 which includes (a) a biostable or biodisintegrable medical device substrate 110, (b) a first discontinuous therapeutic layer 121 disposed on the substrate 110, (c) a biostable and/or biodisintegrable first nanoparticle-derived nanoporous layer 131 on the first therapeutic layer 121 (and on a portion of the substrate 110), (d) a second discontinuous therapeutic layer 122 disposed on the first nanoparticle-derived nanoporous layer 131, which is of the same composition as the first discontinuous therapeutic layer 121, (e) a second nanoparticle-derived nanoporous layer 132 disposed on the second discontinuous therapeutic layer 122 (and on a portion of the first nanoparticle-derived nanoporous layer 131), which is of the same composition as the first nanoparticle-derived nanoporous layer 131, (f) a third discontinuous therapeutic layer 123 disposed on the second nanoparticle-derived nanoporous layer 132, which is of a composition that is different from (e.g., because it contains a different therapeutic agent, etc.) that of the first and second discontinuous therapeutic layers 121,122, and (g) a third nanoparticle-derived nanoporous layer 133 disposed over the third discontinuous therapeutic layer 123 (and on a portion of the second nanoparticle-derived nanoporous layer 132), which is of a different composition and/or pore size from that of the first and second nanoparticle-derived nanoporous layers 131,132.

As a specific example, the therapeutic agent in the third discontinuous therapeutic layer 123 may contain a therapeutic agent with a greater hydrated radius than that found in the first and second therapeutic layers 121,122, and the third nanoporous layer 133 may be derived from nanoparticles that have a larger radius than the nanoparticles forming the first and second nanoporous layers 131,132.

As another specific example, a therapeutic agent in the third discontinuous therapeutic layer 123 may be different from that found in the first and second therapeutic layers 121,122, and the first, second and third nanoporous layers 131,132,133 may be derived from a mixture of biodisintegrable and biostable nanoparticles, wherein the ratio of biodisintegrable-to-biostable nanoparticles in the third nanoporous layer 133 is greater than that of the first and second nanoporous layers 131,132.

Figure 7:
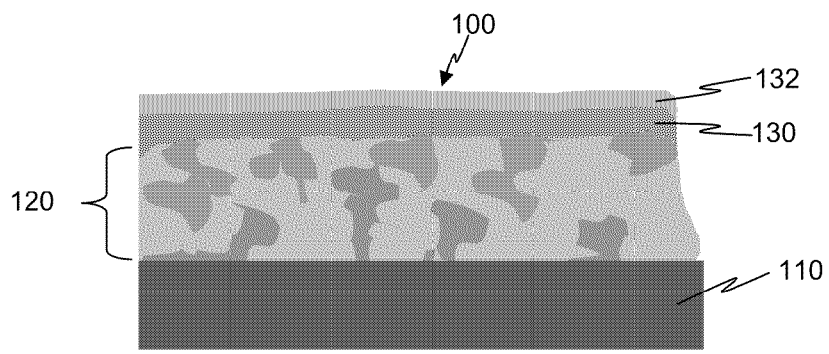

FIG. 7 schematically illustrates a cross-section of a medical device 100 which includes (a) a biostable or biodisintegrable medical device substrate 110, (b) a therapeutic-agent-containing layer 120 disposed over the substrate, (c) a macroporous inorganic layer 130 disposed over the therapeutic-agent-containing layer, and (d) a nanoporous inorganic layer 132 over the macroporous inorganic layer 130.

Figure 7A:
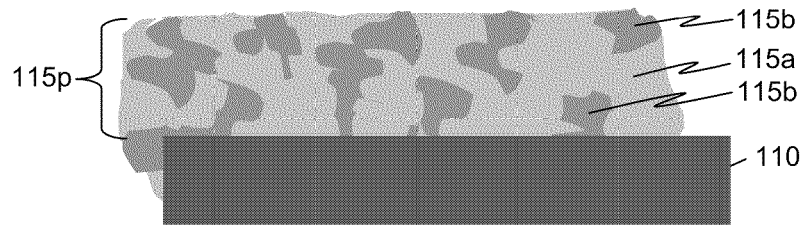
FIGS. 7A-7E are schematic cross-sectional illustrations showing a method of forming the device of FIG. 7.

FIGS. 7A-7E are schematic cross-sectional illustrations showing a method of forming the device of FIG. 7. Turning now to FIG. 7A, in a first step, a reservoir precursor layer 115p is provided over a biostable or biodisintegrable medical device substrate 110. The reservoir precursor layer 115p shown includes a first material component 115a and a second material component 115b. For example, the second material component 115b may be dispersed in the first material component 115a as shown. As another example, first and second material components may constitute interpenetrating networks (not shown). As will be seen below, the primary characteristic of the first and second material components is that the reservoir precursor layer can be subjected to conditions under which at least a portion of the second material component is removed from the reservoir precursor layer such that a porous reservoir layer is formed.

Figure 7B:
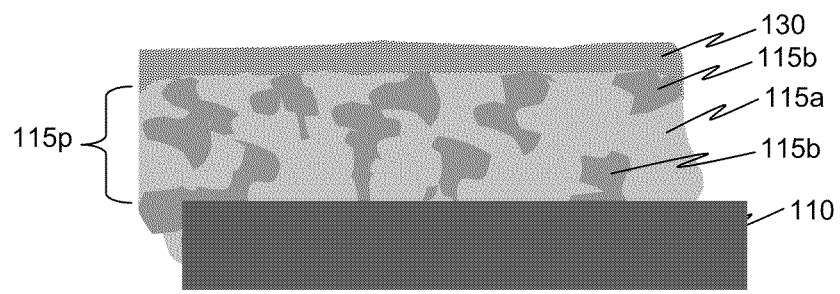

Referring to FIG. 7B, a macroporous layer 130 is then formed over the reservoir precursor layer 115p. For example, the macroporous layer 130 may be formed by processes such as those described herein by which inorganic particles (e.g., the metallic and non-metallic inorganic materials discussed above, among others) are accelerated onto an upper surface of the reservoir precursor layer 115p under conditions by which the inorganic particles become fused and form the macroporous inorganic layer 130. As another example, the macroporous inorganic layer 130 may be created by forming an organic-inorganic composite layer using a block copolymer in combination with sol-gel technology as described in Pub. No. US 2004/0098089 to Weber, followed by heating of the composite layer to create pores. See also A. Jain et al., "Direct Access to Bicontinuous Skeletal Inorganic Plumber's Nightmare Networks from Block Copolymers," *Angew. Chem. Int. Ed.* 2005, 44, 1226-1229.

Figure 7C:
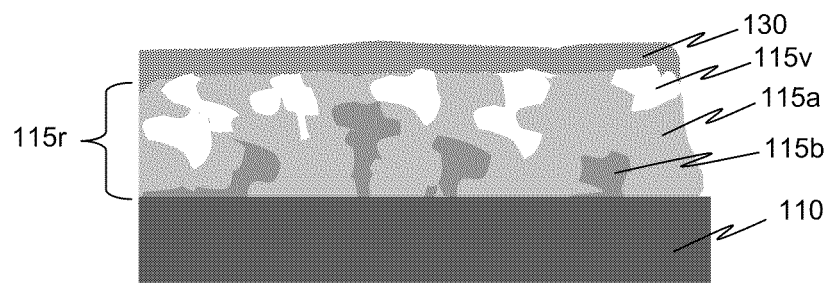

Once a structure like that shown in FIG. 7B is formed, the structure is subjected to conditions such that at least a portion of the second material component 115b is removed from the reservoir precursor layer 115p (which may correspond, for example, to a reduction in volume of the second material component, the complete removal of the second material component, etc.) such that a porous reservoir layer 115r like that shown in FIG. 7C is formed. In the embodiment shown in FIG. 7C, those portions of the second material component 115b lying adjacent to the macroporous inorganic layer 130 are removed to form pores/voids 115v (which can subsequently hold a therapeutic agent, as discussed below), whereas other portions 115b remain within the porous reservoir layer 115r.

In some embodiments, materials that may be used to form the second material component 115b of the reservoir precursor layer 115p may be selected from the following among others: materials that may be at least partially converted to vapor and passed through the macroporous inorganic layer, for instance, evaporable nanoparticles, combustible materials (e.g., materials that react with oxygen to form gaseous by-products such as carbon dioxide and water), sublimable materials (e.g., a sublimable metal such as calcium and magnesium, a sublimable organic compound such as camphor or naphtha, etc.), materials that decrease in volume upon reduction (e.g., certain metal oxides), reducible oxides of sublimable metals (e.g., metal oxides which may be heated under a reducing atmosphere and converted to metals that are sublimable, for instance, oxides of calcium and magnesium). The materials used to form the first material component 115a of the reservoir precursor layer 115p are substantially immune to the forgoing processes (e.g., high melting noble metals such as titanium, high melting and reduction resistant metal oxides, etc.).

In some embodiments, materials that may be used to form the second material component 115b of the reservoir precursor layer 115p include metals that can be oxidized and removed using a suitable removal process. The materials used to form the first material component 115a of the reservoir precursor layer 115p are substantially immune to oxidation and removal. For example, the reservoir precursor layer may be contain a first metal component 115a of higher nobility (e.g., gold, platinum, etc.) and a second metal component 115b of lower nobility (e.g. Zn, Fe, Cu, Ag, etc.). Various methods are available for oxidizing and removing the second metal component 115b, including (a) contact with an appropriate acid (e.g., nitric acid), (b) application of a voltage of sufficient magnitude and bias during immersion in a suitable electrolyte, and (c) heating in the presence of oxygen, followed by dissolution of the resultant oxide.

Reservoir precursor layers 115p with first and second material components 115a, 115b may be formed for example, by combining particles of material that form the first material component 115a with particles of material that form the second material component 115b. A reservoir precursor layer 115p may be formed form such a particle mixture, for example, by causing the particles to consolidate (e.g., by sintering the particle mixture with or without pressure, etc.). Materials are also known which naturally separate into first and second material components having the above characteristics. For example, metal alloys are known which naturally separate into metal phases of lesser and greater nobility. Further information these and other materials can be found in Pub. No. US 2006/0129215 to Helmus et al. and the references cited therein.

Figure 7D:
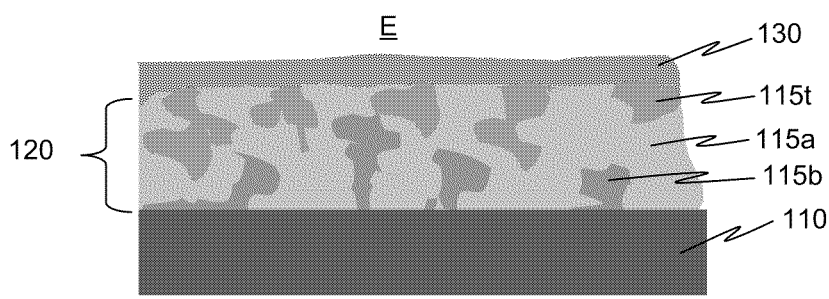

Once a suitable porous reservoir layer 115r like that shown in FIG. 7C is formed, the porous reservoir layer 115r can be loaded with a therapeutic agent. For example, a loading composition comprising a therapeutic agent may be transported from the exterior of the device structure E, through the macroporous inorganic layer 130 such that the pores/voids 115v of FIG. 7C are at least partially filled with a therapeutic composition 115t comprising a therapeutic agent as shown in FIG. 7D. The result of this process is the formation of a therapeutic-agent-containing layer 120, which is made up of the porous reservoir layer 115r and the therapeutic composition 115t within the pores of the porous reservoir layer 115r. Examples of loading compositions include vapor phase compositions that comprise at least one therapeutic agent, which are deposited in the pores of the porous reservoir layer. Examples of loading compositions further include liquid phase compositions that comprise at least one therapeutic agent, for example, melts that comprise at least one therapeutic agent and solutions that comprise at least one therapeutic agent and at least one solvent species. Such liquid phase compositions solidify in pores of the porous reservoir layer upon cooling or by removal of solvent species (e.g., by evaporation).

Figure 7E:
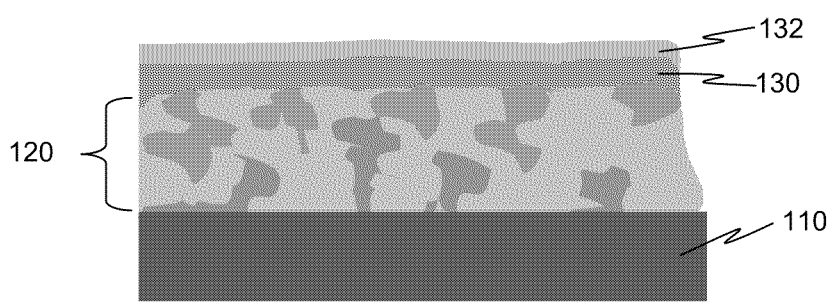

Once a therapeutic-agent-containing layer 120 is formed, a nanoporous layer 132 is formed over the structure of FIG. 7D to form the structure of FIG. 7E. For example, a nanoporous layer 132 may be formed by processes such as those described herein in which inorganic nanoparticles are accelerated onto an upper surface of the macroporous inorganic layer 130 under conditions by which the inorganic nanoparticles become fused and form the nanoporous inorganic layer 132. Examples of materials for the nanoporous inorganic layer 132 include biostable nanoparticles, biodisintegrable nanoparticles, biocatalytic nanoparticles, and combinations thereof, among others.

An advantage of the foregoing method is that, the macroporous inorganic layer 130 is deposited on a precursor to a porous layer (i.e., reservoir precursor layer 115p), rather than on a porous layer. Because such a precursor layer 115p is flatter than a porous counterpart, the macroporous inorganic layer 130 deposition step, and the subsequent nanoporous inorganic layer 132 deposition step, avoid shadow effects which might otherwise allow the therapeutic agent to come out through side gaps. Furthermore deposition on a flat substrate results in an even coating layer which is expected to be better for a uniform therapeutic agent release.

In accordance with certain other embodiments of the invention, biodisintegrable metallic stents are provided. For example, the device may comprise (a) a metallic stent body formed of a first biodisintegrable metal or metal alloy, (b) a therapeutic layer over the stent body, and (c) an inorganic-nanoparticle-derived metallic layer over the therapeutic layer. The metallic layer is formed from a second biodisintegrable metal or metal alloy that may be the same as or different from the first biodisintegrable metal or metal alloy. For instance, the inorganic-nanoparticle-derived metallic layer may be formed from a metal or metal alloy that is more noble than the metal or metal alloy forming the metallic stent body, such that the stent body provides temporary galvanic corrosion protection for the metallic layer. As a specific example, a metallic layer derived from iron nanoparticles may be formed over a therapeutic layer (which may be in the form of a discontinuous layer formed, for example, of islands of therapeutic agent, including distinct deposits, particles, etc.) which is disposed over a stent body formed from magnesium. In some of these embodiments, another an additional iron layer may be deposited over the magnesium stent prior to the therapeutic layer, such that the therapeutic layer is sandwiched between iron layers. As indicated above, the less noble magnesium bulk material of the stent provides galvanic protection against the premature corrosion of the iron layer(s). Consequently, it may be possible to provide a stent in which the drug-containing layer remains present for essentially as long as the bulk stent undergoes corrosion, thus extending therapeutic agent release over essentially the entire life of the magnesium stent, with the iron layer(s) ultimately corroding as well.

In other specific embodiments, inorganic nanoporous layers in accordance with the invention are provided on electrodes for implantable electrical stimulation devices, including leads for pacemakers, implantable cardioverter-defibrillators, spinal cord stimulation systems, deep brain stimulation systems, peripheral nerve stimulation systems, cochlear implants, and retinal implants, among others. Inorganic nanoporous layers in accordance with the invention may be desirable, for example, from a drug release standpoint, a current density standpoint, or both. For instance, steroid-eluting electrodes (e.g., electrodes eluting dexamethasone sodium corticosteroid) are helpful in maintaining the stimulation threshold for pacing. Such systems presently include, for example, impregnated silicone surrounded by a porous titanium electrode that is coated with platinum. In accordance with the present invention, on the other hand, a conductive nanoporous inorganic layer, for example, a nanoporous platinum layer, may be deposited directly onto the silicone. The porosity of the electrodes helps to minimize the size of the electrodes (by maximizing surface area), while maintaining good sensing and stimulation properties. Moreover, the porosity of the electrodes may also help to regulate therapeutic release as well, in the event that a therapeutic agent is provided beneath the nanoporous layer, for example, where the underlying substrate (e.g., silicone, etc.) is impregnated or coated with a therapeutic-agent-containing composition.

In accordance with still other aspects, nanoparticle-derived nanoporous inorganic layers in accordance with the present invention are formed over electroactive polymers (e.g., polypyrrole, among other known electroactive polymers). For examples of medical devices employing electroactive polymers, among others, see, e.g., Pub. Nos. US 2005/0165439, US 2007/0043256 and US 2006/0293563. In such a device, it may be desirable to coat an electroactive polymer with a layer of material that allows the passage of ions into and out of the electroactive polymer (which causes it to expand and contract, thus actuating the device). This function may be provided using inorganic nanoporous layers in accordance with the invention.

"Biologically active agents," "drugs," "therapeutic agents," "pharmaceutically active agents," "pharmaceutically active materials," and other related terms may be used interchangeably herein and include genetic therapeutic agents, non-genetic therapeutic agents and cells. A wide variety of therapeutic agents can be employed in conjunction with the present invention including those used for the treatment of a wide variety of diseases and conditions (i.e., the prevention of a disease or condition, the reduction or elimination of symptoms associated with a disease or condition, or the substantial or complete elimination of a disease or condition). Numerous therapeutic agents are described here.

Suitable non-genetic therapeutic agents for use in connection with the present invention may be selected, for example, from one or more of the following: (a) anti-thrombotic agents such as heparin, heparin derivatives, urokinase, clopidogrel, and PPack (dextrophenylalanine proline arginine chloromethylketone); (b) anti-inflammatory agents such as dexamethasone, prednisolone, corticosterone, budesonide, estrogen, sulfasalazine and mesalamine; (c) antineoplastic/antiproliferative/anti-miotic agents such as paclitaxel, 5-fluorouracil, cisplatin, vinblastine, vincristine, epothilones, endostatin, angiostatin, angiopeptin, monoclonal antibodies capable of blocking smooth muscle cell proliferation, and thymidine kinase inhibitors; (d) anesthetic agents such as lidocaine, bupivacaine and ropivacaine; (e) anti-coagulants such as D-Phe-Pro-Arg chloromethyl ketone, an RGD peptide-containing compound, heparin, hirudin, antithrombin compounds, platelet receptor antagonists, anti-thrombin antibodies, anti-platelet receptor antibodies, aspirin, prostaglandin inhibitors, platelet inhibitors and tick antiplatelet peptides; (f) vascular cell growth promoters such as growth factors, transcriptional activators, and translational promotors; (g) vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; (h) protein kinase and tyrosine kinase inhibitors (e.g., tyrphostins, genistein, quinoxalines); (i) prostacyclin analogs; (j) cholesterol-lowering agents; (k) angiopoietins; (l) antimicrobial agents such as triclosan, cephalosporins, antimicrobial peptides such as magainins, aminoglycosides and nitrofurantoin; (m) cytotoxic agents, cytostatic agents and cell proliferation affectors; (n) vasodilating agents; (o) agents that interfere with endogenous vasoactive mechanisms, (p) inhibitors of leukocyte recruitment, such as monoclonal antibodies; (q) cytokines; (r) hormones; (s) inhibitors of HSP 90 protein (i.e., Heat Shock Protein, which is a molecular chaperone or housekeeping protein and is needed for the stability and function of other client proteins/signal transduction proteins responsible for growth and survival of cells) including geldanamycin, (t) beta-blockers, (u) bARKct inhibitors, (v) phospholamban inhibitors, (w) Serca 2 gene/protein, (x) immune response modifiers including aminoquizolines, for instance, imidazoquinolines such as resiquimod and imiquimod, (y) human apolioproteins (e.g., AI, AII, AIII, AIV, AV, etc.), (z) selective estrogen receptor modulators (SERMs) such as raloxifene, lasofoxifene, arzoxifene, miproxifene, ospemifene, PKS 3741, MF 101 and SR 16234, (aa) PPAR agonists, including PPAR-alpha, gamma and delta agonists, such as rosiglitazone, pioglitazone, netoglitazone, fenofibrate, bexaotene, metaglidasen, rivoglitazone and tesaglitazar, (bb) prostaglandin E agonists, including PGE2 agonists, such as alprostadil or ONO 8815Ly, (cc) thrombin receptor activating peptide (TRAP), (dd) vasopeptidase inhibitors including benazepril, fosinopril, lisinopril, quinapril, ramipril, imidapril, delapril, moexipril and spirapril, (ee) thymosin beta 4, (ff) phospholipids including phosphorylcholine, phosphatidylinositol and phosphatidylcholine, (gg) VLA-4 antagonists and VCAM-1 antagonists.

Preferred non-genetic therapeutic agents include taxanes such as paclitaxel (including particulate forms thereof, for instance, protein-bound paclitaxel particles such as albumin-bound paclitaxel nanoparticles, e.g., ABRAXANE), sirolimus, everolimus, tacrolimus, zotarolimus, Epo D, dexamethasone, estradiol, halofuginone, cilostazole, geldanamycin, alagebrium chloride (ALT-711), ABT-578 (Abbott Laboratories), trapidil, liprostin, Actinomcin D, Resten-NG, Ap-17, abciximab, clopidogrel, Ridogrel, beta-blockers, bARKct inhibitors, phospholamban inhibitors, Serca 2 gene/protein, imiquimod, human apolioproteins (e.g., AI-AV), growth factors (e.g., VEGF-2), as well a derivatives of the forgoing, among others.

Exemplary genetic therapeutic agents for use in connection with the present invention include anti-sense DNA and RNA as well as DNA coding for: (a) anti-sense RNA, (b) tRNA or rRNA to replace defective or deficient endogenous molecules, (c) angiogenic factors including growth factors such as acidic and basic fibroblast growth factors, vascular endothelial growth factor, epidermal growth factor, transforming growth factor α and β, platelet-derived endothelial growth factor, platelet-derived growth factor, tumor necrosis factor α, hepatocyte growth factor and insulin-like growth factor, (d) cell cycle inhibitors including CD inhibitors, and (e) thymidine kinase ("TK") and other agents useful for interfering with cell proliferation. Also of interest is DNA encoding for the family of bone morphogenic proteins ("BMP's"), including BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNA's encoding them.

Vectors for delivery of genetic therapeutic agents include viral vectors such as adenoviruses, gutted adenoviruses, adeno-associated virus, retroviruses, alpha virus (Semliki Forest, Sindbis, etc.), lentiviruses, herpes simplex virus, replication competent viruses (e.g., ONYX-015) and hybrid vectors; and non-viral vectors such as artificial chromosomes and mini-chromosomes, plasmid DNA vectors (e.g., pCOR), cationic polymers (e.g., polyethyleneimine, polyethyleneimine (PEI)), graft copolymers (e.g., polyether-PEI and polyethylene oxide-PEI), neutral polymers PVP, SP1017 (SUPRATEK), lipids such as cationic lipids, liposomes, lipoplexes, nanoparticles, or microparticles, with and without targeting sequences such as the protein transduction domain (PTD).

Cells for use in connection with the present invention include cells of human origin (autologous or allogeneic), including whole bone marrow, bone marrow derived mononuclear cells, progenitor cells (e.g., endothelial progenitor cells), stem cells (e.g., mesenchymal, hematopoietic, neuronal), pluripotent stem cells, fibroblasts, myoblasts, satellite cells, pericytes, cardiomyocytes, skeletal myocytes or macrophage, or from an animal, bacterial or fungal source (xenogeneic), which can be genetically engineered, if desired, to deliver proteins of interest.

Numerous therapeutic agents, not necessarily exclusive of those listed above, have been identified as candidates for vascular and other treatment regimens, for example, as agents targeting restenosis (antirestenotics). Such agents are useful for the practice of the present invention and suitable examples may be selected from one or more of the following: (a) Ca-channel blockers including benzothiazapines such as diltiazem and clentiazem, dihydropyridines such as nifedipine, amlodipine and nicardapine, and phenylalkylamines such as verapamil, (b) serotonin pathway modulators including: 5-HT antagonists such as ketanserin and naftidrofuryl, as well as 5-HT uptake inhibitors such as fluoxetine, (c) cyclic nucleotide pathway agents including phosphodiesterase inhibitors such as cilostazole and dipyridamole, adenylate/Guanylate cyclase stimulants such as forskolin, as well as adenosine analogs, (d) catecholamine modulators including α-antagonists such as prazosin and bunazosine, β-antagonists such as propranolol and α/β-antagonists such as labetalol and carvedilol, (e) endothelin receptor antagonists such as bosentan, sitaxsentan sodium, atrasentan, endonentan, (f) nitric oxide donors/releasing molecules including organic nitrates/nitrites such as nitroglycerin, isosorbide dinitrate and amyl nitrite, inorganic nitroso compounds such as sodium nitroprusside, sydnonimines such as molsidomine and linsidomine, nonoates such as diazenium diolates and NO adducts of alkanediamines, S-nitroso compounds including low molecular weight compounds (e.g., S-nitroso derivatives of captopril, glutathione and N-acetyl penicillamine) and high molecular weight compounds (e.g., S-nitroso derivatives of proteins, peptides, oligosaccharides, polysaccharides, synthetic polymers/oligomers and natural polymers/oligomers), as well as C-nitroso-compounds, O-nitroso-compounds, N-nitroso-compounds and L-arginine, (g) Angiotensin Converting Enzyme (ACE) inhibitors such as cilazapril, fosinopril and enalapril, (h) ATII-receptor antagonists such as saralasin and losartin, (i) platelet adhesion inhibitors such as albumin and polyethylene oxide, (j) platelet aggregation inhibitors including cilostazole, aspirin and thienopyridine (ticlopidine, clopidogrel) and GP IIb/IIIa inhibitors such as abciximab, epitifibatide and tirofiban, (k) coagulation pathway modulators including heparinoids such as heparin, low molecular weight heparin, dextran sulfate and β-cyclodextrin tetradecasulfate, thrombin inhibitors such as hirudin, hirulog, PPACK(D-phe-L-propyl-L-arg-chloromethylketone) and argatroban, FXa inhibitors such as antistatin and TAP (tick anticoagulant peptide), Vitamin K inhibitors such as warfarin, as well as activated protein C, (l) cyclooxygenase pathway inhibitors such as aspirin, ibuprofen, flurbiprofen, indomethacin and sulfinpyrazone, (m) natural and synthetic corticosteroids such as dexamethasone, prednisolone, methprednisolone and hydrocortisone, (n) lipoxygenase pathway inhibitors such as nordihydroguairetic acid and caffeic acid, (o) leukotriene receptor antagonists, (p) antagonists of E- and P-selectins, (q) inhibitors of VCAM-1 and ICAM-1 interactions, (r) prostaglandins and analogs thereof including prostaglandins such as PGE1 and PGI2 and prostacyclin analogs such as ciprostene, epoprostenol, carbacyclin, iloprost and beraprost, (s) macrophage activation preventers including bisphosphonates, (t) HMG-CoA reductase inhibitors such as lovastatin, pravastatin, atorvastatin, fluvastatin, simvastatin and cerivastatin, (u) fish oils and omega-3-fatty acids, (v) free-radical scavengers/antioxidants such as probucol, vitamins C and E, ebselen, trans-retinoic acid, SOD (orgotein) and SOD mimics, verteporfin, rostaporfin, AGI 1067, and M 40419, (w) agents affecting various growth factors including FGF pathway agents such as bFGF antibodies and chimeric fusion proteins, PDGF receptor antagonists such as trapidil, IGF pathway agents including somatostatin analogs such as angiopeptin and ocreotide, TGF-β pathway agents such as polyanionic agents (heparin, fucoidin), decorin, and TGF-β antibodies, EGF pathway agents such as EGF antibodies, receptor antagonists and chimeric fusion proteins, TNF-α pathway agents such as thalidomide and analogs thereof, Thromboxane A2 (TXA2) pathway modulators such as sulotroban, vapiprost, dazoxiben and ridogrel, as well as protein tyrosine kinase inhibitors such as tyrphostin, genistein and quinoxaline derivatives, (x) matrix metalloprotease (MMP) pathway inhibitors such as marimastat, ilomastat, metastat, batimastat, pentosan polysulfate, rebimastat, incyclinide, apratastat, PG 116800, RO 1130830 or ABT 518, (y) cell motility inhibitors such as cytochalasin B, (z) antiproliferative/antineoplastic agents including antimetabolites such as purine analogs (e.g., 6-mercaptopurine or cladribine, which is a chlorinated purine nucleoside analog), pyrimidine analogs (e.g., cytarabine and 5-fluorouracil) and methotrexate, nitrogen mustards, alkyl sulfonates, ethylenimines, antibiotics (e.g., daunorubicin, doxorubicin), nitrosoureas, cisplatin, agents affecting microtubule dynamics (e.g., vinblastine, vincristine, colchicine, Epo D, paclitaxel and epothilone), caspase activators, proteasome inhibitors, angiogenesis inhibitors (e.g., endostatin, angiostatin and squalamine), olimus family drugs (e.g., sirolimus, everolimus, tacrolimus, zotarolimus, etc.), cerivastatin, flavopiridol and suramin, (aa) matrix deposition/organization pathway inhibitors such as halofuginone or other quinazolinone derivatives and tranilast, (bb) endothelialization facilitators such as VEGF and RGD peptide, (cc) blood rheology modulators such as pentoxifylline, and (dd) glucose cross-link breakers such as alagebrium chloride (ALT-711).

Numerous additional therapeutic agents useful for the practice of the present invention are also disclosed in U.S. Pat. No. 5,733,925 to Kunz et al.

Although various embodiments are specifically illustrated and described herein, it will be appreciated that modifications and variations of the present invention are covered by the above teachings and are within the purview of the appended claims without departing from the spirit and intended scope of the invention.

EXAMPLE

Figure 8:
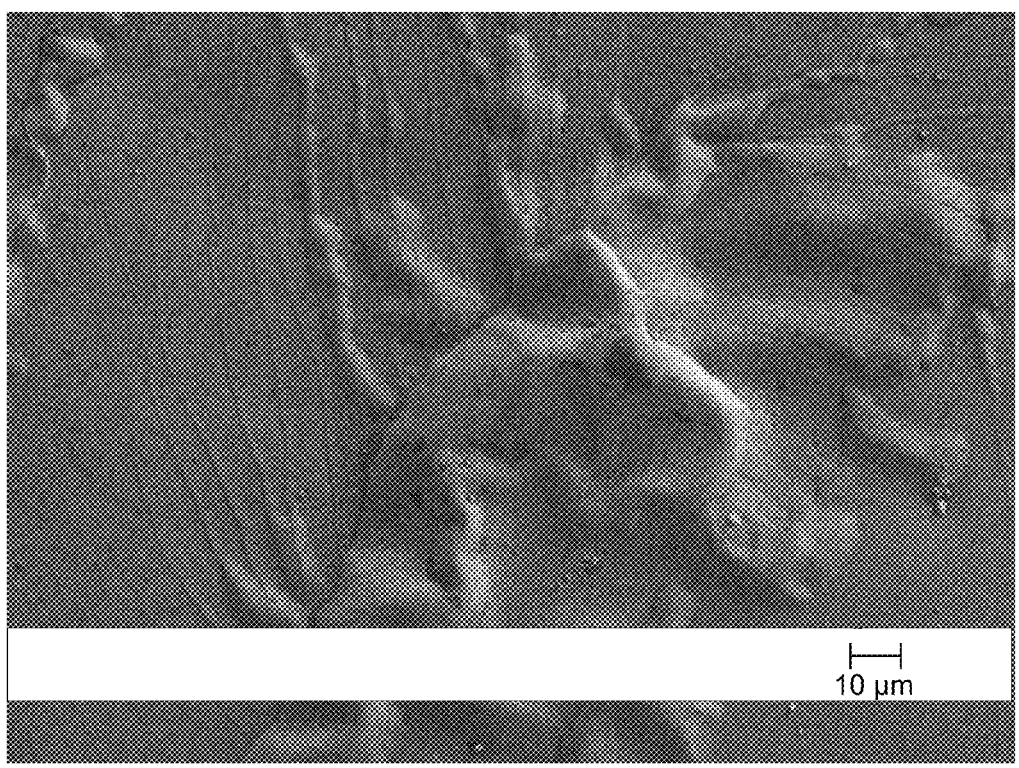
FIG. 8 is a scanning electron micrograph (SEM) of a paclitaxel coated stainless steel substrate, over which an inorganic layer was deposited in accordance with the invention, post drug elution.

Paclitaxel was deposited on a stainless steel substrate (a) by depositing a continuous layer of pure paclitaxel from a solution in THF on a masked substrate (so as to create islands of drug surrounded by bare metal), (b) by depositing a continuous layer of paclitaxel (8.8%) and SIBS (91.2%) from a solution in THF on a masked substrate, or (c) by inkjet deposition of a mixture of 0.005% paclitaxel dissolved in THF onto a the substrate while heating the substrate to 70° C. during deposition, in order to create small amorphous paclitaxel deposits on the surface with areas of exposed bare metal between the deposits. A coating layer of deposited iridium or tantalum nanoparticles was then formed over the paclitaxel deposits using a Mantis Deposition Ltd. system like that described above. Bias voltage was varied between 20 and 4000 V, particle size was varied between 3 and 10 nm, and thickness was varied between 20 and 200 nm. Data analysis indicated that coating thickness had relatively little impact of drug release over the range of thicknesses tested. However, paclitaxel release decreased with increasing bias voltage and decreasing particle size, with the slowest release being observed with inkjet deposited paclitaxel overcoated with a tantalum-nanoparticle-derived layer using a bias voltage of 4000V and a tantalum particle size of approximately 3 nm (coating thickness was 200 nm). The resulting structure exhibited drug elution of 20%~30% in 160 hours with a decaying release function, comparable with current drug eluting stents on the market. A scanning electron micrograph (SEM) of such a coated substrate, post drug elution for 160 hours in PBS/T20 Release Media Solution (0.01 M Phosphate Buffer, 0.05% T20; Sigma PN: P-3563), is shown in FIG. 8. As can be seen from FIG. 8, there is no sign of cracking or delamination in the deposited layer. In general, as paclitaxel elutes, nanoparticle-derived layers were observed to shrink and form folds. The membrane shown in FIG. 8 has not shrunk fully, indicating that paclitaxel is still present underneath the membrane.

Although various embodiments are specifically illustrated and described herein, it will be appreciated that modifications and variations of the present invention are covered by the above teachings and are within the purview of the appended claims without departing from the spirit and intended scope of the invention.

The invention claimed is:

1. A therapeutic-agent releasing medical device made by a method comprising accelerating inorganic nanoparticles onto an upper surface of a structure that comprises (a) a substrate and (b) a therapeutic layer comprising a therapeutic agent disposed over said substrate, said inorganic nanoparticles being accelerated under conditions in which a nanoporous layer comprising fused inorganic nanoparticles is formed over said structure, wherein the therapeutic-agent-containing layer is a discontinuous layer, wherein said inorganic layer is in contact with both the substrate and the therapeutic-agent-containing layer, wherein the inorganic layer is fused to the underlying substrate at positions where the underlying substrate is not covered by the therapeutic-agent-containing layer, wherein the inorganic nanoparticles comprise biostable metallic nanoparticles selected from tantalum nanoparticles and iridium nanoparticles and wherein the average nanoparticle diameter is between 2 and 20 nm in diameter.

2. A medical device comprising a substrate, a therapeutic-agent-containing layer disposed over the substrate, and a nanoporous inorganic layer of fused inorganic nanoparticles disposed over said therapeutic-agent-containing layer, wherein the therapeutic-agent-containing layer is a discontinuous layer, wherein said inorganic layer is in contact with both the substrate and the therapeutic-agent-containing layer, wherein the inorganic layer is fused to the underlying substrate at positions where the underlying substrate is not covered by the therapeutic-agent-containing layer, wherein the inorganic nanoparticles comprise biostable metallic nanoparticles selected from tantalum nanoparticles and iridium nanoparticles and wherein the average nanoparticle diameter is between 2 and 20 nm in diameter.

3. The medical device of claim 2, wherein said therapeutic agent is not present on the outer surface of said inorganic layer.

4. The medical device of claim 2, wherein said substrate and said inorganic layer are formed of the same material.

5. The medical device of claim 2, wherein the therapeutic-agent-containing layer comprises a plurality of islands of therapeutic-agent-containing material disposed on said substrate beneath said inorganic layer.

6. The medical device of claim 2, wherein the therapeutic agent is released from the medical device in vivo in a near zero-order release profile.

7. The medical device of claim 2, wherein the average nanoparticle diameter is between 2 and 15 nm in diameter.

8. The medical device of claim 2, wherein the therapeutic layer comprises paclitaxel.

9. The medical device of claim 2, wherein the thickness of the inorganic layer is at least five times the average diameter of the accelerated nanoparticles.

10. The medical device of claim 2, wherein the biostable metallic nanoparticles are iridium nanoparticles.

11. The medical device of claim 2, wherein the biostable metallic nanoparticles are tantalum nanoparticles.

12. The medical device of claim 2, wherein the therapeutic-agent-containing layer consists essentially of therapeutic agent.

13. The medical device of claim 2, wherein the therapeutic layer further comprises a material selected from polymeric materials, metallic inorganic materials, non-metallic inorganic materials, and combinations thereof.

14. The medical device of claim 2, wherein the therapeutic layer further comprises porous particles.

15. The medical device of claim 2, wherein the medical device is adapted for implantation or insertion into the vasculature, urogenital system, digestive system, or biliary tract.

16. The medical device of claim 2, further comprising an additional therapeutic layer comprising a therapeutic agent over the inorganic layer.

17. The medical device of claim 16, wherein the additional therapeutic layer comprises a therapeutic agent which is not found in the therapeutic layer.

18. The medical device of claim 16, further comprising an additional inorganic layer over the additional therapeutic layer.

19. The medical device of claim 18, wherein the therapeutic agent in the additional therapeutic layer has a greater molecular weight than the therapeutic agent in the therapeutic layer, and wherein the additional inorganic layer has a pore size that is greater than a pore size of the inorganic layer.

20. The medical device of claim 18, wherein the additional inorganic layer is at least partially biodisintegrable and the inorganic layer is biostable.

21. The medical device of claim 18, wherein the additional inorganic layer and the inorganic layer are each formed from a mixture of biostable and biodisintegrable nanoparticles and wherein the ratio of biodisintegrable nanoparticles to biostable nanoparticles is greater in the additional inorganic layer than in the inorganic layer.

22. The medical device of claim 2, wherein the substrate comprises a material selected from polymeric materials, metallic inorganic materials, non-metallic inorganic materials, and combinations thereof.

23. The medical device of claim 2, wherein the substrate is biostable.

24. The medical device of claim 2, wherein the substrate is biodisintegrable.

25. The medical device of claim 2, wherein the substrate is tubular.

26. The medical device of claim 2, wherein the medical device is a stent.

27. The medical device of claim 2, wherein the therapeutic agent is selected from one or more of the group consisting of anti-thrombotic agents, anti-proliferative agents, anti-inflammatory agents, anti-migratory agents, agents affecting extracellular matrix production and organization, antineoplastic agents, anti-mitotic agents, anesthetic agents, anti-coagulants, vascular cell growth promoters, vascular cell growth inhibitors, cholesterol-lowering agents, vasodilating agents, TGF-β elevating agents, and agents that interfere with endogenous vasoactive mechanisms.

28. The medical device of claim 1, wherein the fused nanoparticles have an average diameter of between 2 and 15 nm.

29. The medical device of claim 1, wherein the fused nanoparticles have an average diameter of between 2 and 10 nm.

30. The medical device of claim 2, wherein the fused nanoparticles have an average diameter of between 2 and 10 nm.

31. The medical device of claim 7, wherein the nanoporous layer consists of tantalum nanoparticles.

32. The medical device of claim 30, wherein the nanoporous layer consists of tantalum nanoparticles.

33. The medical device of claim 28, wherein the nanoporous layer consists of iridium nanoparticles.

34. The medical device of claim 29, wherein the nanoporous layer consists of iridium nanoparticles.

35. The medical device of claim 1, wherein said therapeutic agent is not present on the outer surface of said inorganic layer.

36. The medical device of claim 1, wherein the therapeutic-agent-containing layer comprises a plurality of islands of therapeutic-agent-containing material disposed on said substrate beneath said inorganic layer.

37. The medical device of claim 1, wherein the therapeutic agent is released from the medical device in vivo in a near zero-order release profile.

38. The medical device of claim 1, wherein the thickness of the inorganic layer is at least five times the average diameter of the accelerated nanoparticles.

39. The medical device of claim 1, wherein the biostable metallic nanoparticles are iridium nanoparticles.

40. The medical device of claim 1, where the biostable metallic nanoparticles are tantalum nanoparticles.

41. The medical device of claim 1, wherein the therapeutic-agent-containing layer consists essentially of therapeutic agent.

42. The medical device of claim 1, wherein the medical device is adapted for implantation or insertion into the vasculature, urogenital system, digestive system, or biliary tract.

43. The medical device of claim 1, wherein the substrate comprises a material selected from metallic inorganic materials.

44. The medical device of claim 1, wherein the substrate is tubular.

45. The medical device of claim 1, wherein the medical device is a stent.

46. The medical device of claim 1, wherein the therapeutic agent is selected from one or more of the group consisting of anti-thrombotic agents, anti-proliferative agents, anti-inflammatory agents, anti-migratory agents, agents affecting extracellular matrix production and organization, antineoplastic agents, anti-mitotic agents, anesthetic agents, anti-coagulants, vascular cell growth promoters, vascular cell growth inhibitors, cholesterol-lowering agents, vasodilating agents, TGF-β elevating agents, and agents that interfere with endogenous vasoactive mechanisms.

\* \* \* \* \*